United States Patent
Jose et al.

(10) Patent No.: US 10,261,961 B2
(45) Date of Patent: Apr. 16, 2019

(54) METHOD AND APPARATUS FOR REPLICATING DATA ACROSS MULTIPLE DATA CENTERS

(71) Applicant: Change Healthcare Holdings, LLC, Nashville, TN (US)

(72) Inventors: Boban Jose, San Ramon, CA (US); Senthil Kumarasamy, Superior, CO (US)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 445 days.

(21) Appl. No.: 15/073,236

(22) Filed: Mar. 17, 2016

(65) Prior Publication Data
US 2017/0270148 A1 Sep. 21, 2017

(51) Int. Cl.
G06F 16/00 (2019.01)
G06F 16/27 (2019.01)
G16H 10/60 (2018.01)
G06F 19/00 (2018.01)

(52) U.S. Cl.
CPC ............ G06F 16/273 (2019.01); G06F 19/00 (2013.01); G16H 10/60 (2018.01)

(58) Field of Classification Search
CPC ............ G06F 19/322; G06F 17/30578; G06F 16/273; G06F 19/00; G16H 10/60
USPC .......................................................... 707/614
See application file for complete search history.

(56) References Cited

U.S. PATENT DOCUMENTS

| | | | | |
|---|---|---|---|---|
| 7,778,972 B1* | 8/2010 | Cormie | ............. | G06F 17/30094 707/626 |
| 2010/0268844 A1* | 10/2010 | Quinlan | .................... | G06F 9/52 709/238 |
| 2011/0208695 A1* | 8/2011 | Anand | ............. | G06F 17/30578 707/610 |
| 2013/0325824 A1* | 12/2013 | Shoens | ............. | G06F 17/30115 707/698 |
| 2014/0067759 A1* | 3/2014 | Aguilera | ........... | G06F 17/30212 707/610 |
| 2014/0250067 A1* | 9/2014 | Calkowski | ........ | G06F 17/30174 707/624 |

* cited by examiner

*Primary Examiner* — Evan Aspinwall
(74) *Attorney, Agent, or Firm* — Alston & Bird LLP (57) ABSTRACT

A method, computing device and computer program product are provided according to an example embodiment in order to replicate data, and more particularly, to replicate data between data centers while ensuring data consistency, where all participating data centers have both read and write capabilities for the data stored among them. According to an example embodiment, a replication framework including a replication client and replicator service, may include processing circuitry configured to: receive at least one revised data element at the replication client; retrieve a first version identification of a first existing data element stored in a first data center corresponding to the revised data element; cause the revised data element to be stored at a first data center, replacing the corresponding first existing data element; generate a replication event including the revised data element and the version identification; and receive, at the replicator service, the replication event.

20 Claims, 5 Drawing Sheets

METHOD AND APPARATUS FOR REPLICATING DATA ACROSS MULTIPLE DATA CENTERS

TECHNOLOGICAL FIELD

An example embodiment of the present invention relates generally to replicating data, and more particularly, to replicating and synchronizing data between data centers while ensuring data consistency, where each data center has both read and write authority for the data stored therein.

BACKGROUND

A variety of different types of records may be stored in an electronic format so as to facilitate the identification, retrieval and sharing of the records while correspondingly reducing the need for physical records. A network of data centers may be implemented in a variety of embodiments in which data may be shared among the various data centers. Often, data is replicated across two or more data centers such that it is accessible locally from each data center without requiring communication with other, remotely located data centers, which can introduce unwanted latency. The replication of data across data centers can be time consuming and error prone, and can introduce complexity to the retention of data records that is undesirable.

In many cases, data centers operating collaboratively with one another may store data that is written to the memory of a single data center. A single data center may control the read and/or write access to a data record stored on a plurality of data centers, requiring changes to the data, regardless of where received, to be communicated to the data center with read and write access. This process can be arduous and potentially result in data records that are not accurate or current.

BRIEF SUMMARY

A method, computing device and computer program product are provided according to an example embodiment in order to replicate data, and more particularly, to replicate data between data centers while ensuring data consistency, where all participating data centers have both read and write capabilities for the data stored among them. According to an example embodiment, a replication framework including a replication client and replicator service, may include processing circuitry configured to: receive at least one revised data element at the replication client; retrieve a first version identification of a first existing data element stored in a first data center corresponding to the revised data element; cause the revised data element to be stored at a first data center, replacing the corresponding first existing data element; generate a replication event including the revised data element and the version identification; and receive, at the replicator service, the replication event. Embodiments may further be configured to publish, by the replicator service, the replication event to one or more subscribing data centers including the second data center; cause the second data center to retrieve a second version identification of a second existing data element stored in the second data center corresponding to the revised data element; cause the second data center to store the revised data element replacing the second existing data element stored therein in response to the second version identification matching the first version identification; and cause the second data center to not store the revised data element in response to the second version identification not matching the first version identification.

According to some embodiments, the processing circuitry may further be configured to generate a first hash value in response to causing the revised data element to be stored at the first data center; cause a second hash value to be generated in response to causing the revised data element to be stored at the second data center; and cause the replication event to be qualified as successful in response to the first hash value being equivalent to the second hash value. The processing circuitry may further be configured to cause the replication event to be qualified as unsuccessful in response to the first hash value being different from the second hash value. The processing circuitry may further be configured to cause a message to be provided to the replicator service indicating that the replication event was either successful or unsuccessful.

According to some embodiments, the processing circuitry may be configured to reprocess the replication event and publish the replication event for the second data center in response to receiving a message indicating that the replication event was unsuccessful. The revised data element may be received at the replication client via a records interface application configured to enable creation, editing, and deletion of data records stored in the first data center. An alert may be provided from the replication client via the records interface application in response to the replication event being qualified as unsuccessful with respect to the second data center. The processing circuitry may further be configured to send, by the replication client, the replication event to a message queue, where the replicator service retrieves the replication event from the message queue; or, publish, by the replication client, the replication event to a service message bus to which the replicator service is subscribed.

Embodiments of the present invention may provide a method including: receiving at least one revised data element at a replication client; retrieving a first version identification of a first existing data element stored in a first data center corresponding to the revised data element; causing the revised data element to be stored at a first data center, replacing the corresponding first existing data element; generating a replication event including the revised data element and the first version identification; receiving, at a replicator service, the replication event; and publishing, by the replicator service, the replication event to one or more subscribing data centers including a second data center. Methods may include causing the second data center to retrieve a second version identification of a second existing data element stored in the second data center corresponding to the revised data element; causing the second data center to store the revised data element, replacing the second existing data element stored therein in response to the second version identification matching the first version identification; and causing the second data center to not store the revised data element in response to the second version identification not matching the first version identification.

Methods may include: generating a first hash value in response to causing the revised data element to be stored at the first data center; causing a second hash value to be generated in response to causing the revised data element to be stored at the second data center; and causing the replication event to be qualified as successful in response to the first hash value being equivalent to the second hash value. Methods may optionally include causing the replication event to be qualified as unsuccessful in response to the first hash value being different from the second hash value. Methods may include causing a message to be provided to the replicator service indicating that the replication event was either successful or unsuccessful. In response to receiving a message indicating that the replication event was unsuccessful, methods may provide for reprocessing the replication event and publishing the replication event for the second data center.

According to some embodiments, the revised data element may be received at the replication client via a record interface application configured to enable creation, editing, and deletion of data records stored in the first data center, and an alert may be provided from the replication client via the records interface application in response to the replication event being qualified as unsuccessful with respect to the second data center. Methods may include sending, by the replication client, the replication event to a message queue, where the replicator service retrieves the replication event from the message queue; or publishing, by the replication client, the replication event to a service message bus to which the replicator service is subscribed.

Embodiments of the present invention may provide a computer program product including a non-transitory computer readable storage medium having computer program code portions stored thereon. The program code portions may be configured to, upon execution, to: receive at least one revised data element at a replication client; retrieve a first version identification of a first existing data element stored in a first data center corresponding to the revised data element; cause the revised data element to be stored at the first data center, replacing the first existing data element; generate a replication event including the revised data element and the first version identification; receive, at a replicator service, the replication event; and publish, by the replicator service, the replication event to more or more subscribing data centers including a second data center. The program code portions may further be configured to: cause the second data center to retrieve a second version identification of a second existing data element stored in the second data center corresponding to the revised data element; cause the second data center to store the revised data element, replacing the second existing data element stored therein in response to the second version identification matching the first version identification; and cause the second data center to not store the revised data element in response to the second version identification not matching the first version identification.

According to some embodiments, the computer program product may include program code instructions configured, upon execution, to: generate a first hash value in response to causing the revised data element to be stored at the first data center; cause a second hash value to be generated in response to causing the revised data element to be stored at the second data center; and cause the replication event to be qualified as successful in response to the first hash value being equivalent to the second hash value. Embodiments may include program code instructions to cause the replication event to be qualified as unsuccessful in response to the first hash value being different from the second hash value. The program code instructions may further be configured to cause a message to be provided to the replicator service indicating that the replication event was either successful or unsuccessful.

According to some embodiments, the computer program product may include program code instructions configured, upon execution, to reprocess the replication event and publish the replication event for the second data center in response to receiving a message indicating that the replication event was unsuccessful. The revised data element may be received at the replication client via a records interface application configured to enable creation, editing, and deletion of data records stored in the first data center, and an alert may be provided from the replication client via the records interface application in response to the replication event being qualified as unsuccessful with respect to the second data center.

BRIEF DESCRIPTION OF THE DRAWINGS

Having thus described certain example embodiments of the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Further, the apparatus and method of example embodiments of the present invention will be primarily described in conjunction with medical-imaging applications. It should be understood, however, that the apparatus and method may be utilized in conjunction with a variety of other applications, both in the medical industry and outside the medical industry. Like numbers refer to like elements throughout.

A method, computing device and computer program product are provided in accordance with an example embodiment in order to synchronize and replicate data across multiple data centers, enabling read and write privileges to multiple authorities while ensuring the data maintained across the multiple data centers is updated, accurate, and complete. In this regard, the method, computing device, and computer program product of the example embodiment, while described herein primarily in a healthcare data environment, may be implemented in a variety of different data environments, such as tax records, employment records, criminal records, student records or any other type of structured data where data is stored across multiple data centers, and each data center may be accessed for reading and writing data, individually.

One type of record that is being increasingly stored in an electronic format is a patient record. A patient record may be maintained by a healthcare facility, such as in a data center, and may include information regarding a patient, such as various demographic attributes of the patient, e.g., name, address, date of birth, etc., and encounters of the patient with the healthcare facility (i.e., appointments, procedures, etc.). A patient record may also include or be associated with other information, such as one or more documents related to the patient's healthcare including, for example, the physician's notes, lab results and/or images of the patient, e.g., x-rays, magnetic resonance imaging (MRI) images, computer aided tomography (CAT) scans, etc.

Some patients may visit multiple healthcare facilities over the course of time. These healthcare facilities may be owned and operated by different healthcare organizations, or be separate entities within a healthcare organization. Each healthcare facility may maintain a patient record, but the patient records maintained by the different healthcare facilities may be independent of one another since the different healthcare organizations that own and operate the healthcare facilities may not share patient records or otherwise cooperate to maintain a common patient record.

In order to have a more complete and comprehensive understanding of a patient's health, a physician or other healthcare practitioner may wish to have access to all of the patient records, regardless of the healthcare facility that created and maintains the patient records, and to be able to read and/or write data to a patient record. However, in an instance in which a patient has visited multiple healthcare facilities that are owned or operated by different healthcare organizations, and unless the patient has collected and provides a physician or other healthcare practitioner with all of their patient records from the various healthcare facilities that they have visited, the physician or other healthcare practitioner may have difficulty accessing or be unable to access the plurality of patient records maintained for the patient by the various healthcare facilities. The healthcare provider may also have difficulty updating remotely stored patient records of different healthcare facilities with information obtained at a most recent visit. Maintaining different records across different healthcare data centers may prove problematic when attempting to diagnose a patient's condition or to properly care for a patient when all of the information about a patient may not be readily available from a single data center.

As such, a healthcare practitioner may find it difficult to readily access all of the patient records created and stored by the various healthcare facilities that have treated the patient in the past, and the accuracy of the various records may differ substantially. Thus, a healthcare practitioner may not have the benefit of the information contained in at least some of the patient records maintained by other healthcare facilities, thereby potentially reducing the efficiency with which the healthcare practitioner may treat a patient.

By way of example, but not of limitation, the method, apparatus and computer program product will be hereinafter described in conjunction with the synchronization and replication of patient healthcare record data in order to ensure data records related to each patient are updated and accurate across the plurality of data centers, regardless of the data center that receives the most recent patient-related data. Synchronizing and replicating data across a plurality of data centers and ensuring consistency may be complex, such that provided herein is a framework configured to handle the task in a manner that is agnostic to the underlying data source. Conventionally, data is created and updated on a single data center (e.g., the "primary" data center) and it may be replicated across one or more other data centers (e.g., "secondary" data centers). However, the ability to read and write data may rest solely with the primary data center, while the secondary data centers merely store echoed copies of the data provided by the primary data center. Such a solution lacks the convenience of multiple data centers each able to update data records and cascade changes to a data record to remotely stored copies of the data record in other data centers.

Embodiments of the present invention provide a replication framework for supporting persisting data into local storage, and sending synchronization events to all other data centers. The replication framework may be running on all participating data centers which listen for the synchronization events from other ones of the participating data centers, and uses those synchronization events to replicate and update data stored on their local, respective data center. Each data center may be capable of both reading and writing changes to data across all of the data centers operating over the replication framework, such that example embodiments described herein can be implemented on any data center within the network.

Figure 1:
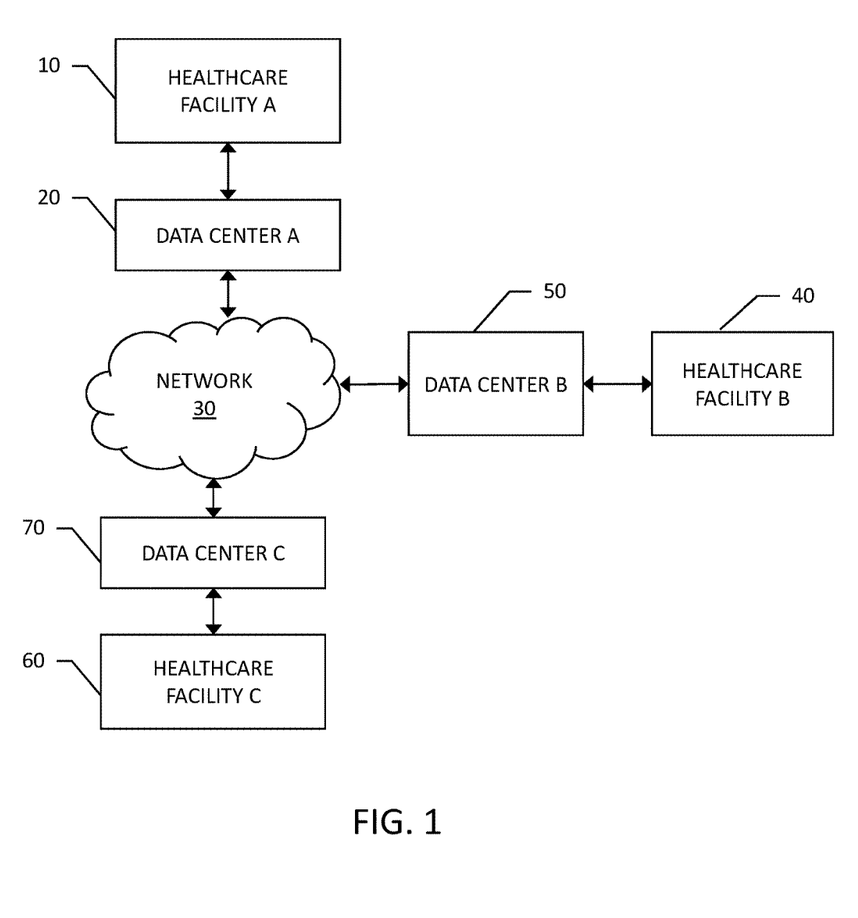
FIG. 1 is a schematic representation of a system for synchronizing and replicating data across multiple data centers in accordance with an example embodiment of the present invention.

While example embodiments described herein may be implemented in various manners, an example embodiment of a network of data centers and related healthcare facilities or systems is illustrated in the block diagram of FIG. 1. The example network infrastructure of FIG. 1 may include a plurality of healthcare facilities, such as healthcare facility A 10, healthcare facility B 40, and healthcare facility C 60. The healthcare facilities shown in FIG. 1 may comprise healthcare systems, hospital systems, local or regional doctor's offices, laboratories that collect/conduct testing on blood, tissue, etc., remote radiological reading facilities, etc. Each healthcare facility represents a facility or system that may edit healthcare records related to a patient, such as during or after a visit from the patient, after a procedure performed on the patient, after a consultation with the patient, based on laboratory results from a patient, etc. The data centers, such as data center A 20, data center B 50, and data center C 70, may represent the data storage centers for each of the respective healthcare facilities. These data centers may be local to a physical location of a healthcare facility, such as a hospital, or may be remote storage locations used by one or more healthcare facilities in a specific healthcare system, such as the physicians of a particular physician network. The data centers of FIG. 1 may be in communication with one another via a network, such as network 30, which will be described further below.

Figure 2:
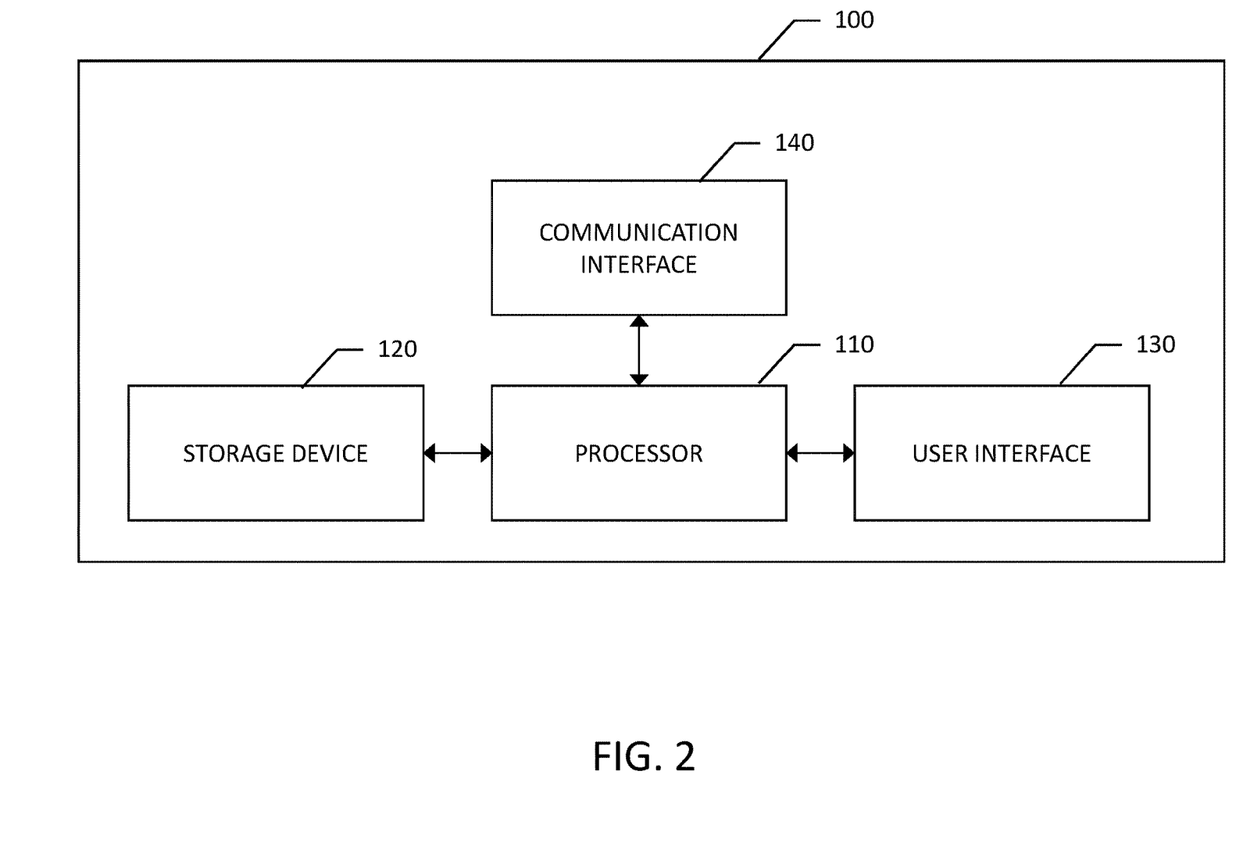
FIG. 2 is a block diagram of a computing device that may be specifically configured in accordance with an example embodiment of the present invention.

FIG. 2 illustrates a block diagram of a computing device 100 in accordance with some example embodiments. The computing device 100 is capable of functioning in a health information infrastructure and may be embodied by one or more servers, computer workstations, desktop or laptop computers or the like, and may be representative of one or more of the data centers (20, 50, 70) of FIG. 1. As described below, the computing device 100 may be configured to implement and/or otherwise support implementation of various example embodiments. However, it should be noted that the components, devices or elements illustrated in and described with respect to FIG. 2 below may not be mandatory and thus some may be omitted in certain embodiments. Additionally, some embodiments may include further or different components, devices or elements beyond those illustrated in and described with respect to FIG. 2.

The computing device 100 may include or otherwise be in communication with processing circuitry of processor 110 that may be configured to perform actions in accordance with one or more example embodiments disclosed herein. In this regard, the processing circuitry may be configured to perform and/or control performance of one or more functionalities of the computing device 100 in accordance with various example embodiments, and thus may provide means for performing functionalities of the computing device. The processor 110 may be configured to perform data processing, application execution and/or other processing and management services according to one or more example embodiments.

In some example embodiments, computing device 100 may include storage device 120, such as a memory, and the processor 110 may be in communication with or otherwise control a communication interface 140 and, in some embodiments, a user interface 130. As such, the processor 110 may be embodied as a circuit chip (e.g., an integrated circuit chip) configured (e.g., with hardware, software or a combination of hardware and software) to perform operations described herein.

The processor 110 may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computing device 100 as described herein.

According to some embodiments, the plurality of processors may be embodied on a single computing device or distributed across a plurality of computing devices collectively configured to function as the computing device 100. In some example embodiments, the processor may be configured to execute instructions stored in the storage device 120 or otherwise accessible to the processor. As such, whether configured by hardware or by a combination of hardware and software, the processor may represent an entity (e.g., physically embodied in circuitry—in the form of processor 110) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

In some example embodiments, the storage device 120 may include one or more non-transitory memory devices such as, for example, volatile and/or non-volatile memory that may be either fixed or removable. In this regard, the storage device may comprise a non-transitory computer-readable storage medium. It will be appreciated that while the storage device 120 is illustrated as a single memory, the storage device may comprise a plurality of memories. The plurality of memories may be embodied on a single computing device or may be distributed across a plurality of computing devices collectively configured to function as the computing device 100. The storage device 120 may be configured to store information, data, applications, instructions and/or the like for enabling the computing device to carry out various functions in accordance with one or more example embodiments. For example, the storage device may be configured to buffer input data for processing by the processor 110. Additionally or alternatively, the storage device 120 may be configured to store instructions for execution by the processor. As yet another alternative, the storage device may include one or more databases that may store a variety of files, contents or data sets, such as patient healthcare records of one or more of the data centers of FIG. 1. Among the contents of the storage device 120, applications may be stored for execution by the processor 110 in order to carry out the functionality associated with each respective application. In some cases, the storage device 120 may be in communication with one or more of the processor 110, user interface 130, or communication interface 140 via a bus or buses for passing information among components of the computing device 100.

The user interface 130 may be in communication with the processor 110 to receive an indication of a user input at the user interface and/or to provide an audible, visual, mechanical or other output to the user. As such, the user interface may include, for example, a keyboard, a mouse, a joystick, a display, a touch screen display, a microphone, a speaker, a Light Emitting Diode (LED), a lighting device, an electronic sensor for capturing human body movements, and/or other input/output mechanisms. In embodiments in which the computing device 100 is implemented on a server, aspects of the user interface may be limited, or the user interface may even be eliminated. For example, the computing device 100 may act as a server or host device (e.g., as data center A 20), with a user interface provided by a client application (e.g., at healthcare facility A 10). The user interface according to some embodiments may present a records interface application, which may be executed by processor 110. The records interface application may enable a user to create, edit, or delete data records stored in a data center, such as on storage device 120. The records interface application may further provide indications to a user of a successful replication event, or an alert that a replication event was unsuccessful, as will be described further below. The records interface application may be a unique application interface specifically configured to enable data replication across multiple data centers using the replication framework described herein. As such, the records interface application may be substantially more than a generic computer for performing generic computer functions. This application facilitates the solution described herein to the networked data center-centric challenge for replicating data accurately among a plurality of data centers, while enabling each data center read and write capabilities.

The communication interface 140 may include one or more interface mechanisms for enabling communication with other devices and/or networks, such as with the healthcare facilities and with other data centers. In this regard, communication with the healthcare facilities includes communication with one or more computing devices (e.g., data centers) of the respective healthcare facilities. In some cases, the communication interface 140 may be any means such as a device or circuitry embodied in either hardware, or a combination of hardware and software that is configured to receive and/or transmit data from/to a network and/or any other device or module in communication with the processor 110. By way of example, the communication interface may be configured to enable the computing device 100 to communicate with the healthcare facilities 10, 40, and 60 and data centers thereof 20, 50, and 70, via a wireless network, such as a wireless local area network (WLAN), cellular network, and/or the like. Additionally or alternatively, the communication interface 140 may be configured to enable the computing device 100 to communicate with the healthcare facilities and data centers via a wire-line network. In some example embodiments, the communication interface 140 may be configured to enable communication between the computing device and one or more healthcare facilities via the internet. Accordingly, the communication interface may, for example, include an antenna (or multiple antennas) and supporting hardware and/or software for enabling communications with a wireless communication network (e.g., a wireless local area network, cellular network, and/or the like) and/or a communication modem or other hardware/software for supporting communication via cable, digital subscriber line (DSL), universal serial bus (USB), Ethernet or other methods.

Having now described computing device 100 configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Embodiments of the present invention may provide a replication framework that supports replicating messages across multiple data centers. The replication framework of example embodiments may include three main components: a replication client, a replicator service, and a reconciliation tool. Each of which may be embodied as one or more computing devices 100 as shown in FIG. 2. An application that may require replication and synchronization, such as a healthcare data records application, may use the replication client. The replication client may persist the data (e.g., using processor 110) into local storage (e.g., storage device 120) of a local data center, then send (e.g., via communication interface 140) a replication event to a message queue. The replicator service, which may be deployed on all participating data centers (e.g., at other healthcare facilities), may listen to the replication events in the message queue. The replicator service may publish the replication events from the message queue via a communication interface to all of the subscribing data centers. An application at each participating data center may listen to these events (i.e., when they are received via a respective communication interface) and call the replication client of their respective data center to persist the replication event into the data center, and send a confirmation or a "replicated event" signaling the successful (or unsuccessful) synchronization and replication of the replication event at their respective data center. The replication service may listen and process the replicated events, which may be tracked by the reconciliation tool. Successful replication messages (e.g., replicated events that signify a successful replication of the data to their respective data center) may be removed from a tracking log of the reconciliation tool as successful events require no further action. The tracking log may be stored on the storage device 120 of the data center originating the replication event. Unsuccessful replication messages (e.g., replicated events that signify an unsuccessful replication of the data to their respective data center) may be marked as failed with additional information regarding the failure to the reconciliation tool to prompt reprocessing of the replication event. The reconciliation tool may provide support to track, monitor, and reprocess the failed events.

Figure 3:
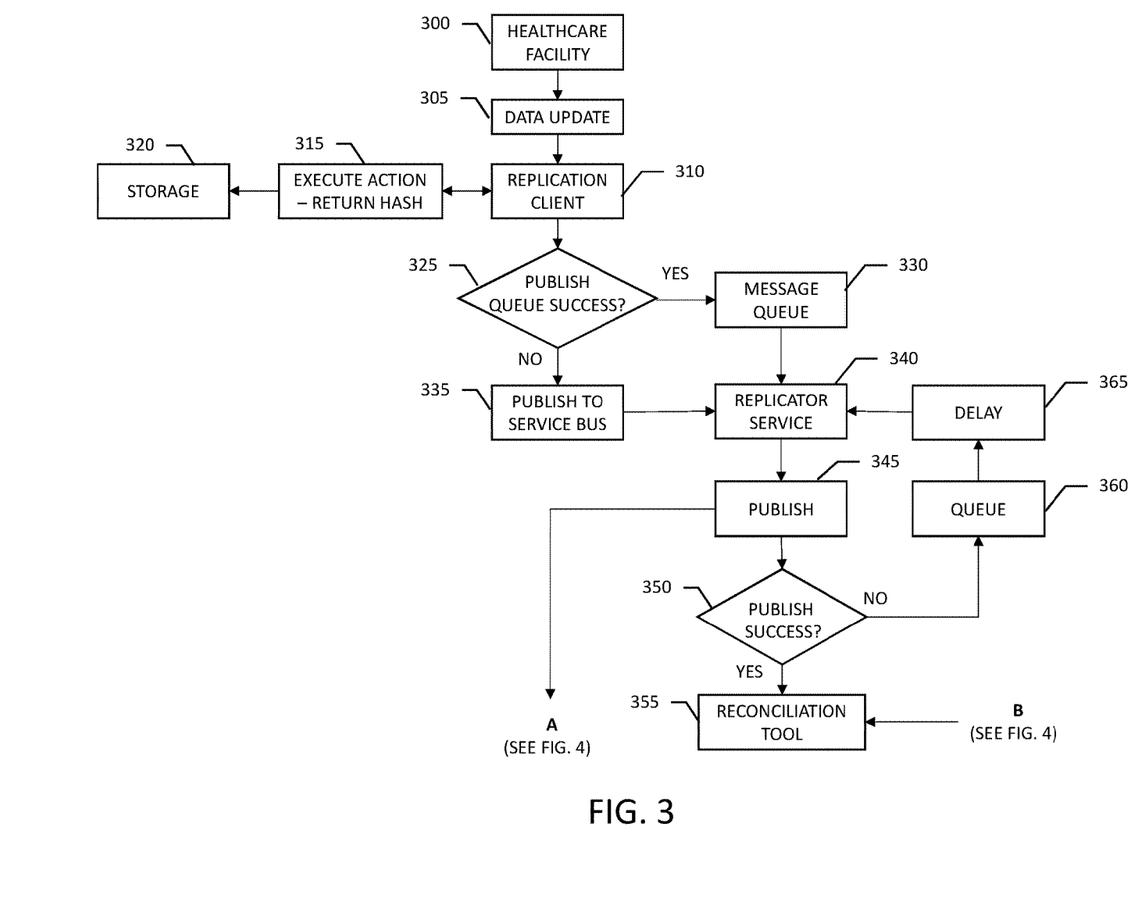
FIG. 3 is a flowchart illustrating operations performed, such as by a computing device of FIG. 2 operating as at least a portion of a replication framework, in conjunction with synchronizing and replicating data across data centers in accordance with an example embodiment of the present invention.

FIG. 3 illustrates a flowchart of the operations of a replication framework for replicating and synchronizing data across multiple data centers. The process begins with an application at a healthcare facility 300 in which patient data is updated at 305, such as via a communication interface 140 of FIG. 2. The replication client at 310 causes the data update to be provided, by action 315, to storage 320, such as storage device 120. Prior to storing the data update, a version of the existing data stored, for example in storage device 120, may be retrieved via processor 110 indicative of the data that is being updated or replaced. This version of the now "old" data may be used to confirm updates to data that are replicated and synchronized across one or more other data centers. The execution of the storage action by the replication client, such as by processor 110, causes a hash (e.g., a hash value) to be returned to the replication client at 315 and 310. The hash returned may be generated based on data in the record, such as a patient record, and may correspond to the revised data element that is replacing the old data. The hash value, together with the version information of the old data, may provide an indication of both the new data (by using the hash value), and the data that is being supplanted by the data update (by using the version information).

The data update, together with the version information and hash value returned through storage 320 at, for example a first data center, becomes a replication event, which is provided for publication at 325, and may be published via communication interface 140, whereupon successful publication results in adding the replication event to a replication event message queue at 330. An unsuccessful addition of the replication event to the message queue may result in the replication event being published to a service bus at 335 as a back-up method for publishing the replication event. Optionally, a publishing service may re-try publication of a message to a message queue a predetermined number of times before seeking an alternate method of publication of the replication event. Further, the service bus publication may be the primary form of publication of a replication event in some embodiments.

Once the replication event is published, to either the queue 330, which may be embodied by storage device 120, or service bus 335, the replicator service 340, which may be operating via processor 110, may pull the message from the queue (or service bus) and push the message to the destination, such as using communication interface 140 and/or processor 110, which may be one or more other data centers, as shown at the publish operation 345. If the publication at 345 is a success, at 350 (e.g., if the replication event is successfully received by the one or more other data centers), the operation continues as described below with respect to FIG. 4, and the reconciliation tool adds the replication event publication to a successful message queue at 355 for later confirmation of successful replication, described further below. If the publication of the replication event to the one or more other data centers fails, at 350, the replication event enters a failed message queue at 360, which may be stored in storage device 120, and is delayed at 365 before returning to the replicator service 340 for another attempt at publication to the one or more other data centers at 345.

Figure 4:
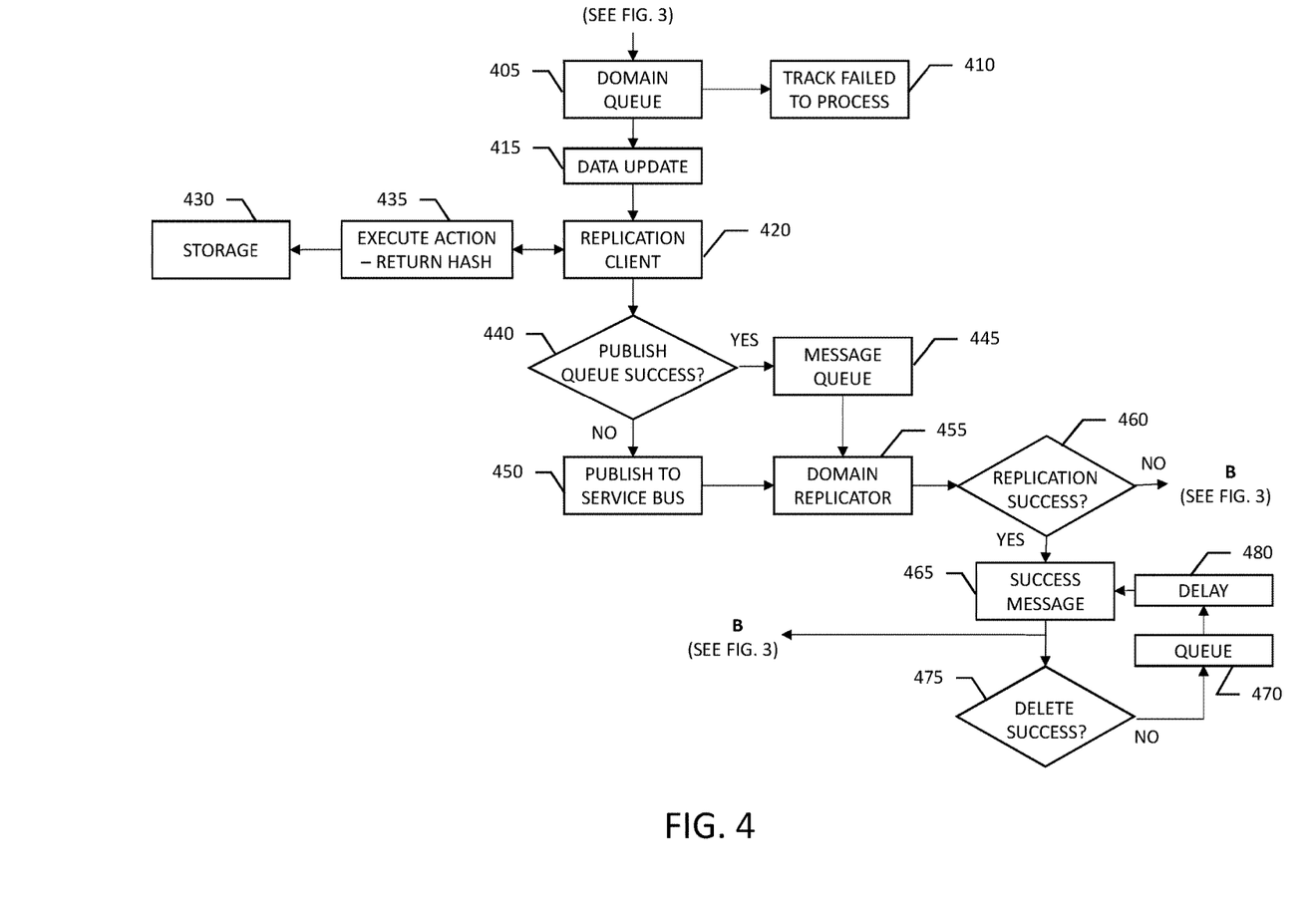
FIG. 4 is a flowchart illustrating operations performed, such as by a computing device of FIG. 2 operating as at least another portion of a replication framework, in conjunction with synchronizing and replicating data across data centers in accordance with an example embodiment of the present invention.

FIG. 4 represents the operations of a replication framework at the one or more other data centers, where a replication event is received, such as via communications interface 140 of the respective data center at a domain queue 405, which may be embodied by storage device 120. If the replication event fails to enter the domain queue at 405, a failure is logged at 410. This failure may be recognized at the first data center, for example, through a lack of a confirmation message being returned to the communication interface 140 of the first data center reconciliation tool as performed with a successful replication event, described further below. Upon successfully entering the domain queue at 405, the data update of the replication event 415 is sent to replication client as shown at 420. The replication client, using processor 110, may establish version information regarding the data that is to be updated, and compare that version information with the version information of the replication event. Should the version of data on the one or more data centers be different from the version information in the replication event, it would be indicative that different data exists between data centers, and the replication event would fail requiring resolution, such as manual intervention, to establish the reason for the failure and inconsistency across data centers. Provided the version information at the one or more data centers matches the version information of the replication event (e.g., the version of the "old" information), the replication client executes the action at 435 of storing the data update to storage 430, and a hash is returned from the storage event indicative of the revised data element that was stored. The hash value may be generated in the same manner as the hash value generated at the original data center from which the data update was received. The hash value being related to the revised data received and stored in the recipient data center.

The replication event including the data update and hash returned at 435 may be provided for publication via communication interface 140 at 440, where successful publication is sent to message queue 445, which may be embodied as storage device 120, and failure to publish to the message queue results in publication of the replication event to the service bus 450. The domain replicator receives the replication event, at 455, and establishes whether the replication is a success or not at 460. The hash value generated at 315 from the revised data element stored at the original data center is compared against the hash value generated at 435 to confirm equivalence. If the hash values are the same, the data update has occurred and the revised data element being stored in the storage (e.g., storage device 120) of each data center is the same, and the replication event is considered a success at 460. A successful replication event generates a success message at 465. The success message is sent back to the original data center and replication client illustrated in FIG. 3, and to reconciliation tool 355, which may be embodied by processor 110 or software, for example. The reconciliation tool, upon receiving the success message via communication interface 140 from the one or more data centers receiving the replication event, may then remove both the success message from the one or more other data centers and the success message generated in response to successful publication of the replication event to the one or more other data centers, as the event is complete and no further action is needed.

Referring back to FIG. 4, if a success message generated at 465 confirming success of the replication event at the one or more other data centers fails to be deleted at the reconciliation tool of FIG. 3, the success message may enter a queue at 470 including delay 480 for a later attempt at sending the success message back to the reconciliation tool for deletion. In this manner, as described in the flowcharts of FIGS. 3 and 4, a replication event that is successfully published by a first data center (e.g., the data center operated in accordance with the flowchart of FIG. 3) to the one or more other data centers (e.g., the data center operated in accordance with the flowchart of FIG. 4), and is successfully updated on the one or more other data centers can be deleted.

If a replication event is unsuccessful at 460 of FIG. 4, for example if the hash generated at the first data center does not match the hash generated at the one or more other data centers, the failure message may be sent by communication interface 140 to reconciliation tool 355. The failed replication event may be flagged for manual review using user interface 130, as it may represent differences in data stored across multiple data centers that may require manual intervention for correction.

While some failed replication events are described herein to solicit manual intervention for resolution, according to some embodiments, failed replication events may be resolved automatically. Failures of replication events may be categorized by the reason for the failure, and may be resolved based on their reason for failure. For example, a failed replication event where the failure was caused by a data version discrepancy (e.g., where the version of the "old" data being replaced from a first data center did not match the version of data being replaced on another data center) may be resolved through a determination of the most recent version of the data, and forcing a replication event using that data, without requiring a version match.

Figure 5:
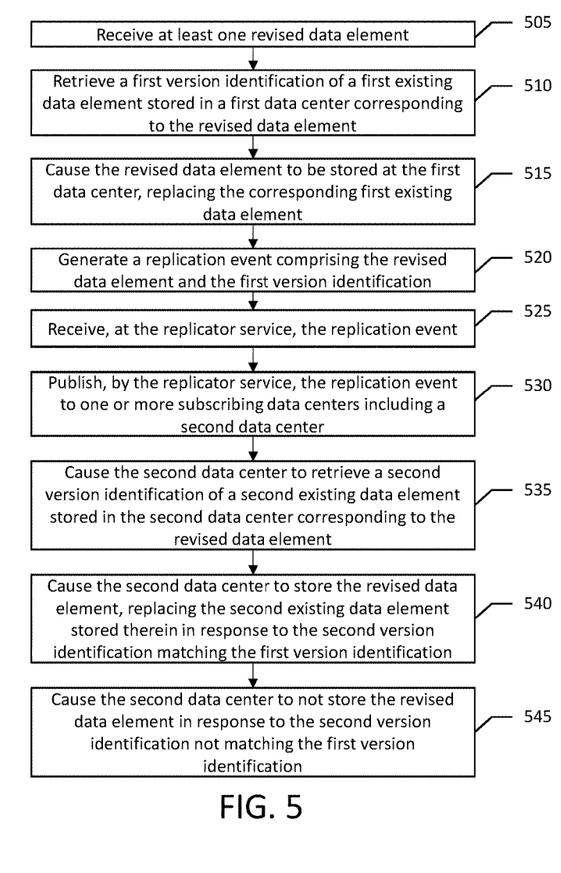
FIG. 5 is a flowchart illustrating a process flow for a successful replication event between two or more data centers according to an example embodiment of the present invention.

Embodiments of the present invention may be illustrated through a flowchart, such as the flowchart of FIG. 5, which depicts a more concise flow of a successful replication event process. As shown in block 505, at least one revised data element is received at a first data center. A first version identification of an existing data element stored in the first data center is retrieved at 510 that corresponds with the revised data element. For example, if an address of patient John Doe is the revised data element, a version of the existing address of patient John Doe is retrieved. The revised data element is stored in the first data center, replacing the corresponding first data element at 515. In the aforementioned example, the new address of patient John Doe replaces the old address of the existing data. At 520 a replication event including the revised data element and the first version identification is generated. In addition, a hash may be generated of the revised data element now stored in the first data center. The hash may be included in the replication event.

At 525, the replication event is received at a replicator service. The replication event is then published by the replicator service at 530 to one or more subscribing data centers including a second data center. The second data center retrieves a second version identification of a second existing data element stored in the second data center corresponding to the revised data element at 535. Continuing with the example above, this second existing data element corresponds to the existing address stored in the second data center for patient John Doe in the aforementioned example. The version of this existing data is retrieved for a validation check as described below. The second data center is caused to store the revised data element, replacing the second existing data element stored therein in response to the second version identification matching the first version identification at 540. Said differently, if the version of the existing or old address of patient John Doe stored at the second data center is the same as the version of the old address of John Doe that was replaced on the first data center, the old address is replaced on the second data center with the revised address. The second data center does not store the revised data element in response to the second version identification not matching the first version identification, as shown at 545. If the version of the old address of John Doe on the second data center is different from the version of the old address on the first data center, the address on the second data center is not replaced with the revised information, as the second data center has conflicting information.

In addition, though not shown, if and when the revised data element is stored in the second data center, a second hash may be generated of the revised data element now stored in the second data store. This hash may be compared with the hash included in the replication event to confirm whether the replication process was performed successfully.

As described above, example embodiments presented herein enable the replication of data across multiple data centers, where each data center may be able to both read and write to data stored on any or all of the other data centers. The replication of data across multiple data centers is a complex operation that can often result in data discrepancies and erroneous data; however, replicating data as described herein precludes data discrepancies between data centers and reduces the incidence of erroneous data stored at any of the data centers operating collaboratively.

As described above, FIGS. 3-5 illustrate flowcharts of a system, method, and computer program product according to example embodiments of the invention. It will be understood that each block of the flowcharts, and combinations of blocks in the flowcharts, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more storage devices 120 of a computing device 100 and executed by processor 110 in the computing device. In some embodiments, the computer program instructions comprising the computer program product(s) which embody the procedures described above may be stored by memory devices of a plurality of computing devices.

As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowcharts support combinations of means for performing the specified functions and combinations of steps for performing the specified functions. It will also be understood that one or more blocks of the flowcharts, and combinations of blocks in the flowcharts, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processor 110 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A replication framework comprising a plurality of data centers, a replication client and replicator service, wherein the replication framework comprises processing circuitry configured to:
    receive at least one revised data element from a first data center of the plurality of data centers at the replication client;
    retrieve a first version identification of a first existing data element stored in the first data center corresponding to the revised data element,
    cause the revised data element to be stored at the first data center, replacing the corresponding first existing data element;
    generate a replication event comprising the revised data element and the first version identification of the first existing data element;
    receive, at the replicator service, the replication event;

publish, by the replicator service, the replication event to one or more subscribing data centers of the plurality of data centers including a second data center;

cause the second data center to retrieve a second version identification of a second existing data element stored in the second data center corresponding to the revised data element;

cause the second data center to store the revised data element, replacing the second existing data element stored therein in response to the second version identification of the second existing data element matching the first version identification of the first existing data element; and cause the second data center to not store the revised data element in response to the second version identification of the second existing data element not matching the first version identification of the first existing data element.

2. The replication framework of claim 1, wherein the processing circuitry is further configured to:

generate a first hash value in response to causing the revised data element to be stored at the first data center;

cause a second hash value to be generated in response to causing the revised data element to be stored at the second data center; and cause the replication event to be qualified as successful in response to the first hash value being equivalent to the second hash value.

3. The replication framework of claim 2, wherein the processing circuitry is further configured to cause the replication event to be qualified as unsuccessful in response to the first hash value being different from the second hash value.

4. The replication framework of claim 3, wherein the processing circuitry is further configured to cause a message to be provided to the replicator service indicating that the replication event was either successful or unsuccessful.

5. The replication framework of claim 4, wherein the processing circuitry is further configured to reprocess the replication event and publish the replication event for the second data center in response to receiving a message indicating that the replication event was unsuccessful.

6. The replication framework of claim 4, wherein the revised data element is received at the replication client via a records interface application configured to enable creation, editing, and deletion of data records stored in the first data center, and wherein an alert is provided from the replication client via the records interface application in response to the replication event being qualified as unsuccessful with respect to the second data center.

7. The replication framework of claim 1, wherein the processing circuitry is further configured to perform at least one of:

send, by the replication client, the replication event to a message queue, wherein the replicator service retrieves the replication event from the message queue; or publish, by the replication client, the replication event to a service message bus to which the replicator service is subscribed.

8. A method comprising:

receiving at least one revised data element at a replication client;

retrieving a first version identification of a first existing data element stored in a first data center corresponding to the revised data element, causing the revised data element to be stored at the first data center, replacing the corresponding first existing data element;

generating a replication event comprising the revised data element and the first version identification of the first existing data element;

receiving, at a replicator service, the replication event;

publishing, by the replicator service, the replication event to one or more subscribing data centers including a second data center;

causing the second data center to retrieve a second version identification of a second existing data element stored in the second data center corresponding to the revised data element;

causing the second data center to store the revised data element, replacing the second existing data element stored therein in response to the second version identification of the second existing data element matching the first version identification of the first existing data element; and causing the second data center to not store the revised data element in response to the second version identification of the second existing data element not matching the first version identification of the first existing data element.

9. The method of claim 8, further comprising generating a first hash value in response to causing the revised data element to be stored at the first data center;

causing a second hash value to be generated in response to causing the revised data element to be stored at the second data center; and causing the replication event to be qualified as successful in response to the first hash value being equivalent to the second hash value.

10. The method of claim 9, further comprising:

causing the replication event to be qualified as unsuccessful in response to the first hash value being different from the second hash value.

11. The method of claim 10, further comprising:

causing a message to be provided to the replicator service indicating that the replication event was either successful or unsuccessful.

12. The method of claim 11, wherein in response to receiving a message indicating that the replication event was unsuccessful, reprocessing the replication event and publishing the replication event for the second data center.

13. The method of claim 11, wherein the revised data element is received at the replication client via a records interface application configured to enable creation, editing, and deletion of data records stored in the first data center, and wherein an alert is provided from the replication client via the records interface application in response to the replication event being qualified as unsuccessful with respect to the second data center.

14. The method of claim 11, wherein the method further comprises:

sending, by the replication client, the replication event to a message queue, wherein the replicator service retrieves the replication event from the message queue; or publishing, by the replication client, the replication event to a service message bus to which the replicator service is subscribed.

15. A computer program product comprising a non-transitory computer readable storage medium having program code portions stored thereon, the program code portions configured, upon execution, to:

receive at least one revised data element at a replication client;

retrieve a first version identification of a first existing data element stored in a first data center corresponding to the revised data element, cause the revised data element to be stored at the first data center, replacing the corresponding first existing data element;

generate a replication event comprising the revised data element and the first version identification of the first existing data element;

receive, at a replicator service, the replication event;

publish, by the replicator service, the replication event to one or more subscribing data centers including a second data center;

cause the second data center to retrieve a second version identification of a second existing data element stored in the second data center corresponding to the revised data element;

cause the second data center to store the revised data element, replacing the second existing data element stored therein in response to the second version identification of the second existing data element matching the first version identification of the first existing data element; and cause the second data center to not store the revised data element in response to the second version identification of the second existing data element not matching the first version identification of the first existing data element.

16. The computer program product of claim 15, wherein the program code instructions are further configured, upon execution, to:

generate a first hash value in response to causing the revised data element to be stored at the first data center;

cause a second hash value to be generated in response to causing the revised data element to be stored at the second data center; and cause the replication event to be qualified as successful in response to the first hash value being equivalent to the second hash value.

17. The computer program product of claim 16, wherein the program code instructions are further configured, upon execution, to:

cause the replication event to be qualified as unsuccessful in response to the first hash value being different from the second hash value.

18. The computer program product of claim 17, wherein the program code instructions are further configured, upon execution, to cause a message to be provided to the replicator service indicating that the replication event was either successful or unsuccessful.

19. The computer program product of claim 18, wherein the program code instructions are further configured to reprocess the replication event and publish the replication event for the second data center in response to receiving a message indicating that the replication event was unsuccessful.

20. The computer program product of claim 18, wherein the revised data element is received at the replication client via a records interface application configured to enable creation, editing, and deletion of data records stored in the first data center, and wherein an alert is provided from the replication client via the records interface application in response to the replication event being qualified as unsuccessful with respect to the second data center.

* * * * *